US010100506B2

(12) United States Patent
Sang et al.

(10) Patent No.: US 10,100,506 B2
(45) Date of Patent: Oct. 16, 2018

(54) CENTRAL INTEGRATED NURSING MACHINE

(71) Applicant: SUZHOU ALTON ELECTRICAL & MECHANICAL INDUSTRY CO., LTD., Jiangsu (CN)

(72) Inventors: Shuhua Sang, Jiangsu (CN); Weidong Lu, Jiangsu (CN); Qiang Song, Jiangsu (CN)

(73) Assignee: SUZHOU ALTON ELECTRICAL & MECHANICAL INDUSTRY CO., LTD., Jiangsu (CN)

( * ) Notice: Subject to any disclaimer, the term of this patent is extended or adjusted under 35 U.S.C. 154(b) by 0 days.

(21) Appl. No.: 15/305,885

(22) PCT Filed: Apr. 3, 2015

(86) PCT No.: PCT/CN2015/075856
§ 371 (c)(1),
(2) Date: Oct. 21, 2016

(87) PCT Pub. No.: WO2015/180532
PCT Pub. Date: Dec. 3, 2015

(65) Prior Publication Data
US 2017/0049649 A1    Feb. 23, 2017

(30) Foreign Application Priority Data

May 26, 2014    (CN) .......................... 2014 1 0225544

(51) Int. Cl.
*E03F 1/00*      (2006.01)
*A47K 10/48*    (2006.01)
*A61G 9/00*     (2006.01)

(52) U.S. Cl.
CPC .............. *E03F 1/006* (2013.01); *A47K 10/48* (2013.01); *A61G 9/003* (2013.01)

(58) Field of Classification Search
CPC ......... E03F 1/006; A47K 10/48; A61G 9/003; A61G 9/00; A61G 9/02; A61F 5/451; A61F 5/44
(Continued)

(56) References Cited

U.S. PATENT DOCUMENTS 3,626,941 A * 12/1971 Webb ........................ A47K 7/08
604/10
5,681,297 A * 10/1997 Hashimoto ............. A61F 5/451
119/164
(Continued)

FOREIGN PATENT DOCUMENTS

CN          1562395         1/2005
CN        101912332        12/2010
(Continued)

OTHER PUBLICATIONS

"Processor" Merriam-Webster.com. Merriam-Webster, Apr. 2018.*
(Continued)

*Primary Examiner* — Benjamin R Shaw
(74) *Attorney, Agent, or Firm* — Barnes & Thornburg LLP; Jeffrey R. Stone (57) ABSTRACT

A central integrated nursing machine includes a main unit and a plurality of working heads, wherein the main unit is provided with a sewage suction device, a water supply device, a main unit processor and a main unit communication module, the sewage suction device is provided with a sewage discharging pipe connected with a sewer, the water supply device is provided with a water taking pipe connected with a tap water source, and the main unit processor is connected with the sewage suction device, the water supply device and the main unit communication module through circuits, respectively; and a plurality of working heads are connected with the sewage suction device and the water supply device on the main unit through pipelines, (Continued)

respectively, and the plurality of working heads are connected with the main unit communication module on the main unit through data transmission interfaces, respectively.

10 Claims, 6 Drawing Sheets

(58) Field of Classification Search
USPC .................................... 4/321, 322, 421, 450
See application file for complete search history.

(56) References Cited

U.S. PATENT DOCUMENTS

| | | | | |
|---|---|---|---|---|
| 5,702,536 | A * | 12/1997 | Carruth | A61G 7/02 134/10 |
| 6,330,725 | B1 * | 12/2001 | Karlsson | B60R 15/04 4/316 |
| 6,554,817 | B1 * | 4/2003 | Oki | A61F 5/451 4/455 |
| 6,651,267 | B1 | 11/2003 | Utz | |
| 2001/0003353 | A1 * | 6/2001 | Kawamoto | A47K 7/04 239/310 |
| 2007/0032765 | A1 * | 2/2007 | Honda | A61F 5/451 604/347 |
| 2007/0199139 | A1 * | 8/2007 | Mueller | E03F 1/006 4/431 |
| 2008/0178377 | A1 * | 7/2008 | Liu | A47K 11/02 4/450 |
| 2009/0074518 | A1 * | 3/2009 | Mueller | B64D 11/02 406/124 |
| 2009/0193571 | A1 * | 8/2009 | Nakamura | A61G 7/02 4/300 |
| 2009/0193572 | A1 * | 8/2009 | Nakamura | A61G 9/00 4/319 |
| 2009/0193573 | A1 * | 8/2009 | Nakamura | A61G 7/02 4/320 |
| 2011/0060300 | A1 * | 3/2011 | Weig | A61F 5/451 604/319 |
| 2011/0064586 | A1 * | 3/2011 | Matsumiya | A61F 5/451 417/36 |
| 2011/0270203 | A1 * | 11/2011 | Sharpe | A61F 5/451 604/326 |
| 2011/0308017 | A1 * | 12/2011 | Nakamura | A61G 7/02 5/605 |
| 2012/0110725 | A1 * | 5/2012 | Lee | A61G 9/00 4/321 |
| 2012/0233758 | A1 * | 9/2012 | Tolles | E03F 1/006 4/321 |
| 2013/0158489 | A1 * | 6/2013 | Ying | A61F 5/451 604/355 |
| 2015/0328072 | A1 * | 11/2015 | Saitoh | A61F 5/451 4/457 |
| 2016/0101007 | A1 * | 4/2016 | Onoda | A61F 5/451 604/326 |
| 2016/0136338 | A1 * | 5/2016 | Lee | A61M 3/06 604/319 |
| 2016/0310313 | A1 * | 10/2016 | Saitoh | A61G 9/00 |

FOREIGN PATENT DOCUMENTS

| | | |
|---|---|---|
| CN | 102293702 | 12/2011 |
| CN | 202892179 | 4/2013 |
| CN | 203169480 | 9/2013 |
| CN | 103655094 | 3/2014 |
| CN | 103989563 | 8/2014 |
| CN | 204016705 | 12/2014 |
| EP | 1312329 | 5/2003 |
| JP | 56-135729 | 3/1980 |
| JP | 3161991 | 8/2010 |
| JP | 2013-212353 | 10/2013 |

OTHER PUBLICATIONS

"Process" Merriam-Webster.com. Merriam-Webster, Apr. 2018.*
Extended European Search Report dated May 3, 2017, for EP 15800670.0, filed Apr. 3, 2015.

* cited by examiner

CENTRAL INTEGRATED NURSING MACHINE

TECHNICAL FIELD

The present disclosure relates to the technical field of medical nursing appliances, and particularly to a central integrated nursing machine.

BACKGROUND

With the development of people' living standards, sickbed patients unable to defecate and urinate by themselves due to cardiovascular and cerebrovascular diseases and other diseases are increasing year by year, which brings great pressure to the family and the society; the patients cannot defecate by themselves, so assistance from accompanying persons is needed; and however, the workload of the accompanying persons is increased due to uncertainty of a defecation time of the patients, and great pain and burden are brought to physiology and particularly spirit of the patients. Therefore, medical institutions and patients families often use a special urination or defecation nursing machine to reduce the burden of nursing persons, thereby effectively improving a therapy environment of the patients.

In the present market, a common urination or defecation nursing machine includes a working head and a main unit. The working head is sheathed on a lower body of the patient for collecting excrement, a water spraying mechanism is arranged on the working head to wash the lower body of the patient and clean interior of the working head, and a blower is further arranged on the working head for drying the surface of the lower body of the patient. The main unit is provided with a clean water pail, a water heating device, a sewage pail and a negative pressure source, wherein water stored in the clean water pail is heated by the water heating device and then conveyed to the water spray mechanism through a water pump, and the negative pressure source vacuumizes the sewage pail so as to suck the excrement in the working head connected with the sewage pail into the sewage pail. In occasions where the bedridden patients are concentrated such as nursing homes and hospitals, the main unit of the existing nursing machine when in use is repeatedly configured, a large space is occupied, and a lot of circuits and pipelines are arranged in a sickroom, leading to waste of resources and great safety danger. The clean water pail and the sewage pail on the nursing machine are limited in volume; in order to avoid the shutdown of the nursing machine, each nursing machine needs to be filled with water and to discharge the sewage regularly and quantitatively by a nursing assistant, which greatly increases the workload of the nursing assistant.

SUMMARY

An objective of the present disclosure is to provide a central integrated nursing machine, which overcomes defects and weaknesses in the prior art and is reasonable in structure, convenient to use, and capable of effectively saving the configuration cost of the nursing machine and reducing the workload of a nursing assistant.

In order to achieve the above-mentioned objective, the present disclosure adopts a technical solution as follows.

A central integrated nursing machine provided in the present disclosure includes a main unit and a plurality of working heads, wherein the main unit is provided with a sewage suction device, a water supply device, a main unit processor and a main unit communication module, the sewage suction device is provided with a sewage discharging pipe for connecting with a sewer, the water supply device is provided with a water taking pipe for connecting with a tap water source, and the main unit processor is connected with the sewage suction device, the water supply device and the main unit communication module through circuits, respectively; and the plurality of working heads are connected with the sewage suction device and the water supply device on the main unit through pipelines, respectively, and the plurality of working heads are connected with the main unit communication module on the main unit through data transmission interfaces, respectively.

Further, the sewage suction device includes a sewage pail and a negative pressure source, wherein the sewage pail is connected with the negative pressure source through an air pipe, and the sewage pail is provided with the sewage discharging pipe for connecting with the sewer; and the sewage pail is provided with a sewage selector, the plurality of working heads are connected with the sewage selector through water pipes, respectively, and the main unit processor is connected with the sewage selector through a circuit.

Further, the air pipe between the sewage pail and the negative pressure source is provided with a water removal device, the water removal device includes a base and a water storage cup, an upper end of the base is provided with an air inlet connecting pipe and an air outlet connecting pipe, the water storage cup is arranged at a lower end of the base corresponding to the air inlet connecting pipe, the water storage cup is provided with a first sensor for detecting a height of liquid level in the water storage cup, the first sensor is connected with the main unit processor through a circuit, and a lower end of the water storage cup is provided with a water discharging switch; and a water separation ball matched with the air outlet connecting pipe is arranged in the base, an upper end of the air outlet connecting pipe is provided with a filter, the air inlet connecting pipe is connected with the sewage pail through a water pipe, and the air outlet connecting pipe is connected with the negative pressure source through an air pipe.

Further, the sewage discharging pipe is provided with a sewage discharging switch valve, the sewage pail is provided with a second sensor for detecting a height of liquid level in the sewage pail, and the sewage discharging switch valve and the second sensor are connected with the main unit processor through circuits, respectively.

Further, the water supply device includes a heating box, a second shunt valve, a PTC heater, a small water pump, a big water pump and a UV sterilizer, wherein the heating box is provided with the water taking pipe for connecting with the tap water source, the heating box, the second shunt valve, the small water pump, the PTC heater and the UV sterilizer are successively connected with one another through water pipes, and the UV sterilizer is connected with the heating box through a water pipe; and the big water pump is connected with the second shunt valve through a water pipe, the second shunt valve, the PTC heater, the small water pump, the big water pump and the UV sterilizer are connected with the main unit processor through circuits, respectively, and the plurality of working heads are connected with the big water pump through water pipes, respectively.

Further, the big water pump is provided with a clean water selector, the plurality of working heads are connected with the clean water selector through water pipes, respectively, and the clean water selector is connected with the main unit processor through a circuit.

Further, each working head is provided with an excrement container, a drying device, a first shunt valve, an auxiliary unit processor and an auxiliary unit communication module, wherein the excrement containers on the plurality of working heads are connected with the sewage suction device on the main unit through pipelines, respectively, a plurality of washing spray heads are arranged on an inner wall of each excrement container, the plurality of washing spray heads are connected with the first shunt valve, respectively, and the first shunt valves on the plurality of working heads are connected with the water supply device on the main unit through water pipes, respectively; the drying device is arranged on a rear side wall of the excrement container directly facing an opening of the working head, and the auxiliary unit processor is connected with the first shunt valve and the auxiliary unit communication module through circuits, respectively; and the auxiliary unit communication modules on the plurality of working heads are connected with the main unit communication module on the main unit through data transmission interfaces, respectively.

Further, the inner wall of the excrement container is provided with a feces sensor and a urine sensor, and the feces sensor and the urine sensor are connected with the auxiliary unit processor through circuits, respectively.

Further, the plurality of washing spray heads include a sprinkling spray head for spraying to the lower body of a patient, flushing spray heads for spraying to the inner wall of the excrement container and a discharging spray head for spraying towards excrement, wherein the sprinkling spray head, the flushing spray heads and the discharging spray head are connected with the first shunt valve through water pipes, respectively; and the sprinkling spray head is arranged on the rear side wall of the excrement container directly facing the opening of the working head, the flushing spray heads are arranged at two side edges of the opening of the excrement container, the flushing spray heads can translate back and forth along the edges of the opening of the excrement container, and the discharging spray head is arranged on a front edge of the opening of the excrement container.

Further, the first shunt valves on the plurality of working heads are connected with a clean water selector on the main unit through water pipes, respectively, and a sewage discharging opening of the excrement container is connected with the sewage selector through a water pipe.

The present disclosure has the following beneficial effects: by reasonably combining one main unit and a plurality of working heads, the device configuration cost in hospitals or nursing homes is decreased, and the main unit is connected with an original sewer and an original tap water source in the sickroom, thereby avoiding the shutdown problem caused by water shortage and fullness of the sewage pail, requiring no regular cleaning of the nursing assistant, and effectively liberating labor time of the nursing assistant.

10. main unit; 11. main unit processor; 12. main unit communication module;
13. sewage selector; 14. clean water selector; 15. sewage pail; 16. negative pressure source;
17. water taking pipe; 18. sewage discharging pipe; 19. deodorizing assembly;
20. second working head; 21. excrement container; 22. drying device;
23. first shunt valve; 24. auxiliary unit processor;
25. auxiliary unit communication module; 27. feces sensor; 28. urine sensor;
29. sealing valve; 31. sprinkling spray head; 32. flushing spray head;
33. discharging spray head; 40. water removal device;
50. water supply device; 51. heating box; 52. second shunt valve; 53. PTC heater;
54. small water pump; 55. UV sterilizer; 56. big water pump;
151. second sensor; 181. sewage discharging switch valve.

DETAILED DESCRIPTION

The present disclosure is further described below with reference to the attached drawings.

Figure 1:
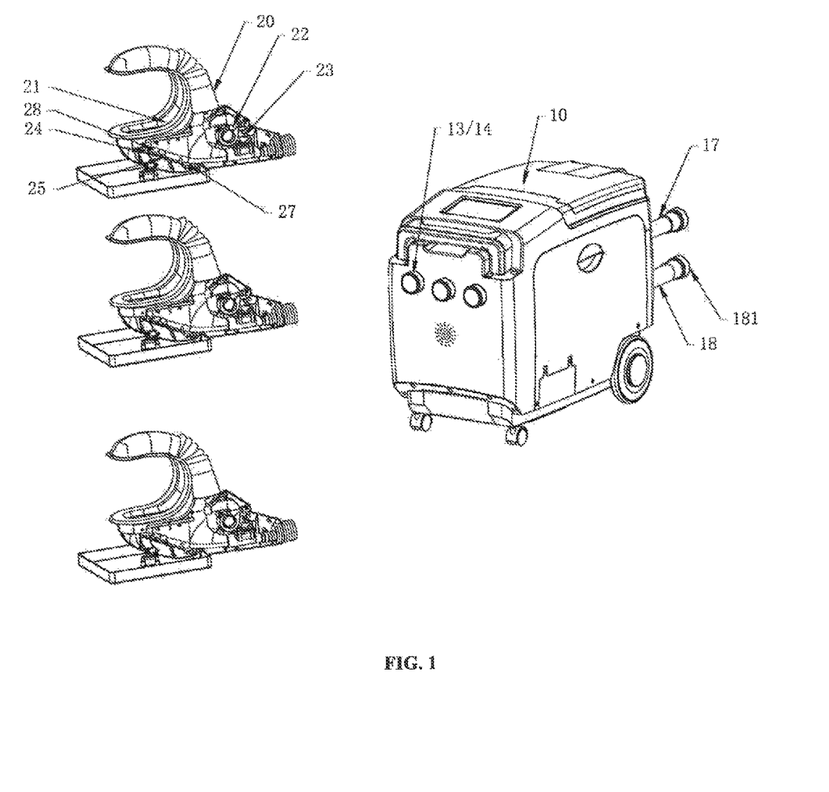
FIG. 1 is an overall structural schematic diagram of the present disclosure.
Figure 6:
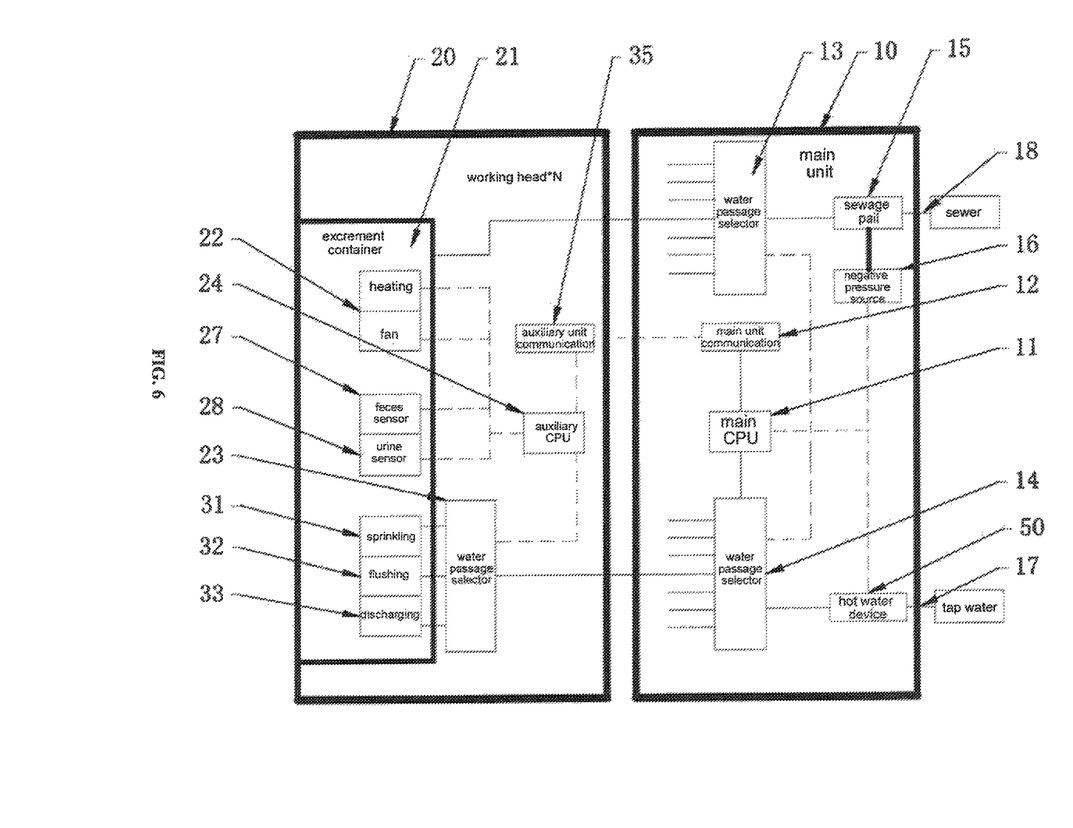
FIG. 6 is a structural schematic diagram showing a connection relationship of various parts of the nursing machine provided in the present disclosure.

A central integrated nursing machine provided in the present disclosure includes a main unit 10 and a plurality of working heads 20, wherein the main unit 10 is provided with a sewage suction device, a water supply device 50, a main unit processor 11 and a main unit communication module 12; the sewage suction device is provided with a sewage discharging pipe 18 for connecting with a sewer; the water supply device is provided with a water taking pipe 17; the main unit processor 11 is connected with the sewage suction device, the water supply device and the main unit communication module 12 through circuits, respectively; the plurality of working heads 20 are connected with the sewage suction device and the water supply device on the main unit 10 through pipelines, respectively; the plurality of working heads 20 are connected with the main unit communication module 12 on the main unit 10 through data transmission interfaces, respectively; the plurality of working heads 20 are each arranged on a sickbed to be connected with the lower body of a patient; each working head 20 is separately connected with the main unit 10 through the pipelines and is operated separately according to a sensing device of the working head 20; after detecting excrement of the patient, the working head 20 transmits a signal to the main unit 10 through the data transmission interface, and the main unit processor 11 controls the sewage suction device and the water supply device 50 to cooperate with the corresponding working head 20 according to the signal of each working head 20; the excrement sucked by the sewage suction device is directly discharged to the sewer through the sewage discharging pipe 18 after flowing in the main unit 10, and the water supply device 50 supplies water directly through the water taking pipe 17 for connecting with a tap water source, so that the shutdown of the main unit 10 caused by the insufficient water stored in the main unit 10 can be prevented from influencing the nursing work of the working heads 20, thereby reducing the workload of the nursing assistant for clearing the excrement and supplementing the water in the main unit 10, and realizing a purpose of unmanned autonomous control and operation.

Figure 3:
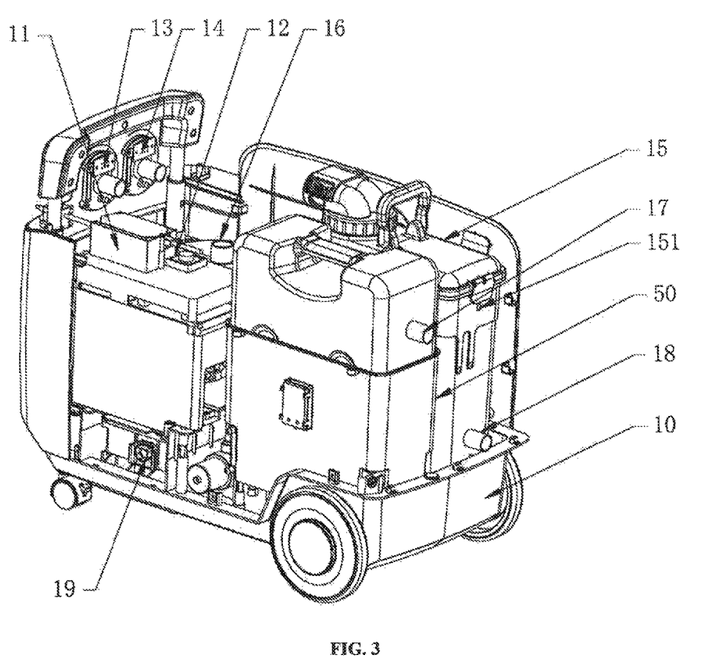
FIG. 3 is a structural schematic diagram showing an interior of a main unit of the present disclosure.
Figure 4:
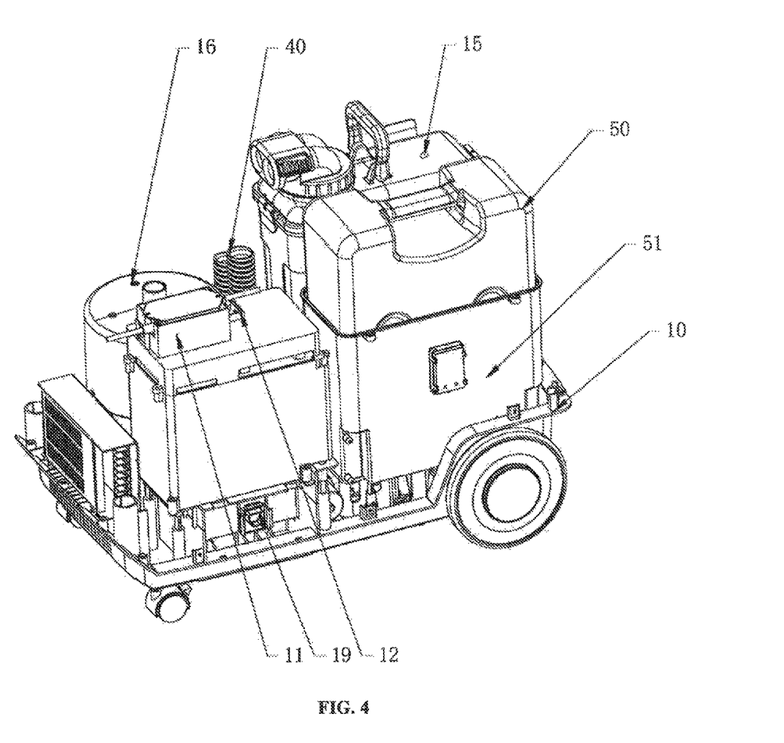
FIG. 4 is a structural schematic diagram showing the interior of the main unit of the present disclosure from another view.

The sewage suction device includes a sewage pail 15 and a negative pressure source 16, wherein the sewage pail 15 is connected with the negative pressure source 16 through an air pipe, the negative pressure source 16 vacuumizes the sewage pail 15 so as to generate negative pressure inside the sewage pail and to suck the excrement in the plurality of working heads 20 connected with the sewage pail 15, the sewage pail 15 is provided with the sewage discharging pipe 18 for connecting with the sewer, the excrement in the sewage pail 15 is discharged to the sewer through the sewage discharging pipe 18, thereby preventing the shutdown of the working heads 20 caused by the fullness of excrement in the sewage pail 15, and reducing the workload of the nursing assistant for regularly checking and cleaning; and the sewage pail 15 is provided with a sewage selector 13, the plurality of working heads 20 are connected with the sewage selector 13 through water pipes, respectively, the main unit processor 11 is connected with the sewage selector 13 through a circuit, and after receiving a signal from the working head 20, the main unit processor 11 controls the sewage selector 13 to enable the sewage pail 15 to connect with the corresponding working head 20, and then the negative pressure source 16 starts up, so that the excrement in the working heads 20 is sucked by the sewage pail 15.

The air pipe between the sewage pail 15 and the negative pressure source 16 is provided with a water removal device 40, the water removal device 40 is configured to remove splashed water and fogging water in the sewage pail 15, thereby preventing the suction of vapor in the negative pressure source 16 from damaging the negative pressure source; the water removal device 40 includes a base and a water storage cup, an upper end of the base is provided with an air inlet connecting pipe and an air outlet connecting pipe, the water storage cup is arranged at a lower end of the base corresponding to the air inlet connecting pipe, the water storage cup is provided with a first sensor for detecting a height of liquid level in the water storage cup, the first sensor is connected with the main unit processor 11 through a circuit, and a lower end of the water storage cup is provided with a water discharging switch; and a water separation ball matched with the air outlet connecting pipe is arranged inside the base, an upper end of the air outlet connecting pipe is provided with a filter, the air inlet connecting pipe is connected with the sewage pail 15 through a water pipe, and the air outlet connecting pipe is connected with the negative pressure source 16 through an air pipe.

The sewage discharging pipe 18 is provided with a sewage discharging switch valve 181, the sewage pail 15 is provided with a second sensor 151 for detecting a height of liquid level in the sewage pail 15, the sewage discharging switch valve 181 and the second sensor 151 are connected with the main unit processor 11 through circuits, respectively, and the sewage discharging switch valve 181 is a normally-closed switch valve. After the second sensor 151 detects and discovers that the liquid surface in the sewage pail 15 is higher than a set height, a signal is transmitted to the main unit processor 11, the main unit processor 11 opens the sewage discharging switch valve 181 to discharge the excrement and cleaning waste water into the sewer, thereby reducing the workload of the nursing assistant for manual intervention and regular routing inspection.

Figure 5:
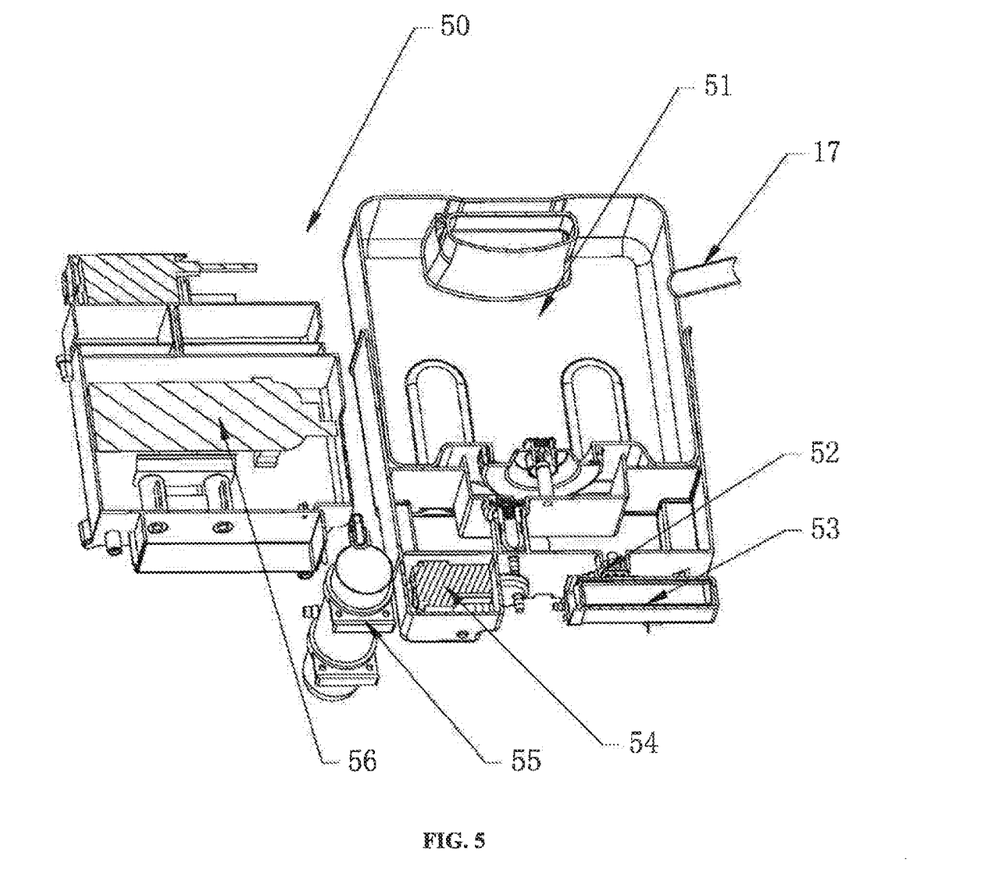
FIG. 5 is a structural schematic diagram showing a partial section of a heating device of the present disclosure.

The water supply device 50 includes a heating box 51, a second shunt valve 52, a PTC heater 53, a small water pump 54, a big water pump 56 and a UV sterilizer 55, wherein the heating box 51 is provided with the water taking pipe 17 for connecting with the tap water source, the heating box 51, the second shunt valve 52, the small water pump 54, the PTC heater 53 and the UV sterilizer 55 are successively connected with one another through water pipes, and the UV sterilizer 55 is connected with the heating box 51 through a water pipe; the big water pump 56 is connected with the second shunt valve 52 and a clean water selector 14 through water pipes, respectively, and the second shunt valve 52, the PTC heater 53, the small water pump 54, the big water pump 56 and the UV sterilizer 55 are connected with the main unit processor 11 through circuits, respectively. The main unit processor 11 receives a corresponding washing signal transmitted from an auxiliary unit processor 24 and opens a water inlet of the heating box 51 to allow clean water in the tap water source to enter the heating box 51, after sufficient clean water is obtained, the water inlet is closed, a passage between the second shunt valve 52 and the small water pump 54 is opened, the clean water in the heating box 51 is pumped by the small water pump 54 and is returned to the heating box 51 after being heated by the PTC heater 53 and sterilized by the UV sterilizer 55, and the water is cycled, so that after the clean water in the heating box 51 is heated to a set temperature, a temperature controller in the heating box 51 transmits a signal to the main unit processor 11, a passage between the second shunt valve 52 and the small water pump 54 is closed, the PTC heater 53 and the UV sterilizer 55 are turned off, the second shunt valve 52 is switched to a passage of the big water pump 56, the big water pump 56 is started up to convey the hot water in the heating box 51 to the clean water selector 14, and the clean water selector 14 opens a passage of a corresponding working head 20 to supply water to the corresponding first shunt valve 23.

Figure 2:
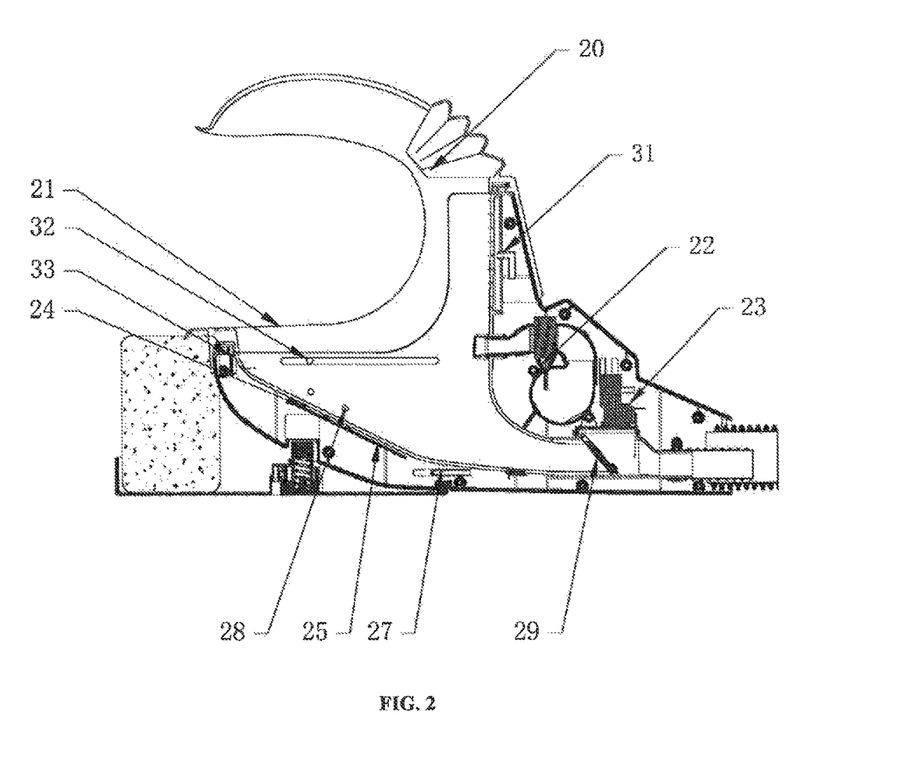
FIG. 2 is a structural schematic diagram showing a section of a working head of the present disclosure.

Each working head 20 is provided with an excrement container 21, a drying device 22, the first shunt valve 23, the auxiliary unit processor 24 and an auxiliary unit communication module 25, wherein the excrement containers 21 on the plurality of working heads 20 are connected with the sewage suction device on the main unit 10 through pipelines, respectively; the working heads 20 transmit signals to the main unit 10, so that the sewage suction device of the main unit is started up to suck the excrement in the excrement containers 21; an inner wall of each excrement container 21 is provided with a plurality of washing spray heads, which are connected with the first shunt valve 23, respectively, the first shunt valve 23 controls the corresponding washing spray head to spray water and wash the interior of the corresponding excrement container 21, and the washing sewage is sucked by the sewage suction device on the main unit 10; the drying device 22 is connected onto a rear side wall of the excrement container 21 directly facing an opening of the working head 20, the drying device 22 generates hot air to be blown towards the lower body of the patient at the excrement container 21, and the drying device 22 is close to the lower body of the patient, so that the drying effect is better, and the comfort of the patient is improved; the first shunt valves 23 on the plurality of working heads 20 are connected with the water supply device 50 on the main unit 10 through water pipes, respectively; the auxiliary unit processor 24 is connected with the first shunt valve 23 and the auxiliary unit communication module 25 through circuits, respectively, and the auxiliary unit processor 24 controls the first shunt valve 23 to select the corresponding spray head so as to execute a washing operation according to a set program; and the auxiliary unit communication modules 25 on the plurality of working heads 20 are connected with the main unit communication module 12 on the main unit 10 through data transmission interfaces, respectively.

The inner wall of the excrement container 21 is provided with a feces sensor 27 and a urine sensor 28, wherein the feces sensor 27 and the urine sensor 28 are connected with the auxiliary unit processor 24 through circuits, respectively; the feces sensor 27 and the urine sensor 28 each detects a type of the excrement of the patient and transmits a corresponding signal to the auxiliary unit processor 24, and after receiving the signal, the auxiliary unit processor 24 transmits a washing execution signal to the main unit 10 through the auxiliary unit communication module 25.

The plurality of washing spray heads include a sprinkling spray head 31 for spraying to the lower body of the patient, flushing spray heads 32 for spraying to the inner wall of the excrement container 21 and a discharging spray head 33 for spraying to the excrement; the sprinkling spray head 31, the flushing spray heads 32 and the discharging spray head 33 are connected with the first shunt valve 23 through water pipes, respectively; and the first shunt valve 23 is controlled by the auxiliary unit processor 24 to select a corresponding passage to supply water to the sprinkling spray head 31, the flushing spray heads 32 or the discharging spray head 33, thereby executing the corresponding washing program.

The sprinkling spray head 31 is arranged on the rear side wall of the excrement container 21 directly facing the opening of the working head 20, the flushing spray heads 32 are arranged at two side edges of the opening of the excrement container 21 and can translate back and forth along the edges of the opening of the excrement container 21, and the discharging spray head 33 is arranged on the front edge of the opening of the excrement container 21.

The first shunt valves 23 on the plurality of working heads 20 are connected with the clean water selector 14 on the main unit 10 through water pipes, respectively, and a sewage discharging opening of the excrement container 21 is connected with the sewage selector 13 through a water pipe.

A sealing valve 29 for preventing back-flow of odor is arranged at a junction between the excrement container 21 and a hose; when the working head 20 is at a non-working state, the sealing valve 29 is at a closed state, thereby blocking a connection passage between the excrement container 21 and the sewage pail 15, and preventing odor of the excrement in the sewage pail 15 from diffusing in the sickroom through the hose and the excrement container 21; and the main unit 10 is provided with a deodorizing assembly 19, which is connected to an air exhaust opening of the negative pressure source 16, the smell emitted by the excrement in the sewage pail 15 is exhausted outwards via the negative pressure source 16 under a vacuumizing effect of the negative pressure source 16, and the exhausted air is deodorized and filtered by the deodorizing assembly 19, thereby preventing the odor from diffusing in the sickroom.

The above only describes preferred embodiments of the present disclosure, so that all equivalent changes or modifications made for the structure, features and the principle according to the application scope of the present disclosure should fall within the application scope of the present disclosure.

What is claimed is:

1. A central integrated nursing machine, comprising a main unit and a plurality of working heads; the main unit is provided with a sewage suction device, a water supply device, a main unit processor and a main unit communication module; the sewage suction device is provided with a sewage discharging pipe for connecting with a sewer; the water supply device is provided with a water taking pipe for connecting with a tap water source; the main unit processor is connected with the sewage suction device, the water supply device and the main unit communication module through circuits, respectively; the plurality of working heads are connected with the sewage suction device and the water supply device on the main unit through pipelines, respectively; and the plurality of working heads are connected with the main unit communication module on the main unit through data transmission interfaces, respectively, wherein the sewage suction device comprises a sewage pail and a negative pressure source; the sewage pail is connected with the negative pressure source through an air pipe, and the sewage pail is provided with the sewage discharging pipe connected with the sewer; and the sewage pail is provided with a sewage selector, the plurality of working heads are connected with the sewage selector through water pipes, respectively, and the main unit processor is connected with the sewage selector through a circuit.

2. The central integrated nursing machine according to claim 1, wherein the air pipe between the sewage pail and the negative pressure source is provided with a water removal device, the water removal device comprises a base and a water storage cup, an upper end of the base is provided with an air inlet connecting pipe and an air outlet connecting pipe, the water storage cup is arranged at a lower end of the base corresponding to the air inlet connecting pipe, the water storage cup is provided with a first sensor for detecting a height of liquid level in the water storage cup, the first sensor is connected with the main unit processor through a circuit, and a lower end of the water storage cup is provided with a water discharging switch; and a water separation ball matched with the air outlet connecting pipe is arranged in the base, an upper end of the air outlet connecting pipe is provided with a filter, the air inlet connecting pipe is connected with the sewage pail through a water pipe, and the air outlet connecting pipe is connected with the negative pressure source through an air pipe.

3. The central integrated nursing machine according to claim 1, wherein the sewage discharging pipe is provided with a sewage discharging switch valve, the sewage suction device comprises a sewage pail, the sewage pail is provided with a second sensor for detecting a height of liquid level in the sewage pail, and the sewage discharging switch valve and the second sensor are connected with the main unit processor through circuits, respectively.

4. A central integrated nursing machine, comprising a main unit and a plurality of working heads; the main unit is provided with a sewage suction device, a water supply device, a main unit processor and a main unit communication module; the sewage suction device is provided with a sewage discharging pipe for connecting with a sewer; the water supply device is provided with a water taking pipe for connecting with a tap water source; the main unit processor is connected with the sewage suction device, the water supply device and the main unit communication module through circuits, respectively; the plurality of working heads are connected with the sewage suction device and the water supply device on the main unit through pipelines, respectively; and the plurality of working heads are connected with the main unit communication module on the main unit through data transmission interfaces, respectively, wherein the water supply device comprises a heating box, a second shunt valve, a PTC heater, a small water pump, a big water pump and a UV sterilizer; the heating box is provided with the water taking pipe connected with the tap water source, the heating box, the second shunt valve, the small water pump, the PTC heater and the UV sterilizer are successively connected with one another through water pipes, and the UV sterilizer is connected with the heating box through a water pipe; and the big water pump is connected with the second shunt valve through a water pipe; the second shunt valve, the PTC heater, the small water pump, the big water pump and the UV sterilizer are connected with the main unit processor through circuits, respectively, and the plurality of working heads are connected with the big water pump through water pipes, respectively.

5. The central integrated nursing machine according to claim 4, wherein the big water pump is provided with a clean water selector, the plurality of working heads are connected with the clean water selector through water pipes, respectively, and the clean water selector is connected with the main unit processor through a circuit.

6. A central integrated nursing machine. comprising a main unit and a plurality of working heads; the main unit is provided with a sewage suction device, a water supply device, a main unit processor and a main unit communication module; the sewage suction device is provided with a sewage discharging pipe for connecting with a sewer; the water supply device is provided with a water taking pipe for connecting with a tap water source; the main unit processor is connected with the sewage suction device, the water supply device and the main unit communication module through circuits, respectively; the plurality of working heads are connected with the sewage suction device and the water supply device on the main unit through pipelines, respectively; and the plurality of working heads are connected with the main unit communication module on the main unit through data transmission interfaces, respectively, wherein each working head is provided with an excrement container, a drying device, a first shunt valve, an auxiliary unit processor and an auxiliary unit communication module; the excrement containers on the plurality of working heads are connected with the sewage suction device on the main unit through pipelines, respectively, a plurality of washing spray heads are arranged on an inner wall of each excrement container, the plurality of washing spray heads are connected with the first shunt valve, respectively, and the first shunt valve on the plurality of working heads is connected with the water supply device on the main unit through water pipes, respectively; the drying device is arranged on a rear side wall of the excrement container directly facing an opening of the working head, and the auxiliary unit processor is connected with the first shunt valve and the auxiliary unit communication module through circuits, respectively; and the auxiliary unit communication modules on the plurality of working heads are connected with the main unit communication module on the main unit through data transmission interfaces, respectively.

7. The central integrated nursing machine according to claim 6, wherein the inner wall of the excrement container is provided with a feces sensor and a urine sensor, and the feces sensor and the urine sensor are connected with the auxiliary unit processor through circuits, respectively.

8. The central integrated nursing machine according to claim 6, wherein the plurality of washing spray heads comprise a sprinkling spray head for spraying to the lower body of a patient, flushing spray heads for spraying to the inner wall of the excrement container, and a discharging spray head for spraying towards excrement; the sprinkling spray head, the flushing spray heads and the discharging spray head are connected with the first shunt valve through water pipes, respectively; and the sprinkling spray head is arranged on the rear side wall of the excrement container directly facing the opening of the working head, the flushing spray heads are arranged at two side edges of the opening of the excrement container, the flushing spray heads can translate back and forth along the edges of the opening of the excrement container, and the discharging spray head is arranged on a front edge of the opening of the excrement container.

9. The central integrated nursing machine according to claim 6, wherein the first shunt valves on the plurality of working heads are connected with a clean water selector on the main unit through water pipes, respectively, and a sewage discharging opening of the excrement container is connected with the sewage selector through a water pipe.

10. A central integrated nursing machine, comprising a main unit and a plurality of working heads; wherein the main unit is provided with a sewage suction device, a water supply device and a main unit processor; the sewage suction device is provided with a sewage discharging pipe for connecting with a sewer; the water supply device is provided with a water taking pipe for connecting with a tap water source; and the plurality of working heads are connected with the sewage suction device and the water supply device on the main unit through pipelines, respectively;

wherein the sewage suction device comprises a sewage pail and a negative pressure source; the sewage pail is connected with the negative pressure source through an air pipe, and the sewage pail is provided with the sewage discharging pipe connected with the sewer; and the sewage pail is provided with a sewage selector, the plurality of working heads are connected with the sewage selector through water pipes, respectively, and the main unit processor is connected with the sewage selector through a circuit.

* * * * *